United States Patent
Hulse et al.

(10) Patent No.: US 8,741,828 B2
(45) Date of Patent: Jun. 3, 2014

(54) AZEOTROPE AND AZEOTROPE-LIKE COMPOSITIONS USEFUL FOR THE PRODUCTION OF HALOOLEFINS

(75) Inventors: Ryan Hulse, Morristown, NJ (US); Hang T. Pham, Morristown, NJ (US); Hsueh Sung Tung, Morristown, NJ (US); Konstantin Pokrovski, Morristown, NJ (US); Daniel C. Merkel, Morristown, NJ (US)

(73) Assignee: Honeywell International Inc., Morristown, NJ (US)

( * ) Notice: Subject to any disclaimer, the term of this patent is extended or adjusted under 35 U.S.C. 154(b) by 94 days.

(21) Appl. No.: 13/355,965

(22) Filed: Jan. 23, 2012

(65) Prior Publication Data
US 2012/0215039 A1    Aug. 23, 2012

Related U.S. Application Data

(60) Provisional application No. 61/445,776, filed on Feb. 23, 2011.

(51) Int. Cl.
*C09K 5/16* (2006.01)
*C07C 17/383* (2006.01)

(52) U.S. Cl.
USPC .......................................... 510/408; 570/160

(58) Field of Classification Search
None
See application file for complete search history.

(56) References Cited

U.S. PATENT DOCUMENTS

| 6,281,396 B1 | 8/2001 | Manzer et al. |
| 2007/0197841 A1 | 8/2007 | Mukhopadhyay et al. |
| 2009/0203945 A1 | 8/2009 | Mukhopadhyay et al. |
| 2009/0224207 A1 | 9/2009 | Pham et al. |
| 2009/0227822 A1 | 9/2009 | Pham et al. |
| 2009/0240090 A1 | 9/2009 | Merkel et al. |
| 2009/0256110 A1* | 10/2009 | Merkel et al. ............ 252/182.12 |
| 2010/0072415 A1 | 3/2010 | Rao et al. |
| 2010/0102273 A1 | 4/2010 | Basu et al. |
| 2010/0113322 A1 | 5/2010 | Tung et al. |
| 2010/0237279 A1 | 9/2010 | Hulse et al. |
| 2011/0155942 A1 | 6/2011 | Pigamo et al. |
| 2011/0160497 A1 | 6/2011 | Deur-Bert et al. |
| 2011/0160499 A1 | 6/2011 | Wendlinger et al. |
| 2011/0218369 A1 | 9/2011 | Elsheikh et al. |
| 2011/0270000 A1 | 11/2011 | Bektesevic et al. |

FOREIGN PATENT DOCUMENTS

WO    2011087825 A1    7/2011

OTHER PUBLICATIONS

PCT Search Report, PCT/US2012/025908. Filed Feb. 21, 2012.
Kim, et al., "A Study to Determine the Existence of an Azeotropic R-22 "Drop-In" Substitute," prepared by U.S. Department of Commerce for Electric Power Research Institute, Mar. 1996, pp. 1-45, U.S.
Morrison, et al., "Azeotropy in Refrigerant Mixtures," International Journal of Refrigeration, 1993, pp. 129-138, vol. 16, No. 2. U.S.

* cited by examiner

*Primary Examiner* — Jafar Parsa
*Assistant Examiner* — Medhanit Bahta
(74) *Attorney, Agent, or Firm* — Scully, Scott, Murphy & Presser, P.C.

(57) ABSTRACT

The present invention pertains to ternary azeotrope and azeotrope-like composition including 2-chloro-3,3,3-trifluoropropene (HCFO-1233xf), HF, and either 1,1,2,3-tetrachloropropene (TCP) or 1,1,1,2,2-pentafluoropropane (HFC-245cb). The present invention also relates to binary azeotropes of 2,3,3,3-tetrachloropropene and HF. Such azeotropic and azeotrope-like compositions are useful as intermediates in the production of 2,3,3,3-tetrafluoropropene (HFO-1234yf).

13 Claims, No Drawings

AZEOTROPE AND AZEOTROPE-LIKE COMPOSITIONS USEFUL FOR THE PRODUCTION OF HALOOLEFINS

CROSS REFERENCES TO RELATED APPLICATIONS

This application is related to and claims the priority benefit of U.S. provisional application No. 61/445,776, filed Feb. 23, 2011, the contents of which are incorporated herein by reference.

FIELD OF THE INVENTION

The present invention pertains to ternary and binary azeotropes and azeotrope-like compositions that are useful in the production of haloolefins.

BACKGROUND OF THE INVENTION

Fluorocarbon based fluids, including chlorofluorocarbons ("CFCs") or hydrochlorofluorocarbons ("HCFCs"), have properties that are desirable in industrial refrigerants, blowing agents, heat transfer media, solvents, gaseous dielectrics, and other applications. For use in these applications, as well as uses in the production of halocarbons, single component fluids or azeotrope-like mixtures, i.e., those which do not substantially fractionate on boiling and evaporation, are particularly desirable.

Unfortunately, suspected environmental problems, such as global warming and ozone depletion, have been attributed to the use of some of these fluids, thereby limiting their contemporary use. Hydrofluoroolefins ("HFOs") have been proposed as possible replacements for such CFCs, HCFCs, and HFCs. The identification of new, environmentally-safe, non-fractionating mixtures comprising HFOs are complicated, however, due to the fact that azeotrope formation is not readily predictable. Therefore, industry is continually seeking new HFO-based mixtures that are acceptable and environmentally safer substitutes for CFCs, HCFCs, and HFCs, which may be used for HFO production or within one or a combination of the foregoing applications. This invention satisfies these needs among others.

SUMMARY OF THE INVENTION

The present invention relates to ternary and binary azeotrope and azeotrope-like compositions, which are useful in the production of haloolefins. In one aspect, the ternary azeotropic or azeotrope-like compositions consist essentially of hydrogen fluoride (HF), 2-chloro-3,3,3-trifluoropropene (HCFO-1233xf), and a third component selected from either 1,1,2,3-tetrachloropropene or 1,1,1,2,2-pentafluoropropane (HFC-245cb). The binary azeotrope or azeotrope-like compositions consist essentially of 2,3,3,3-tetrachloropropene and hydrogen fluoride. While not limited thereto, one or a combination of these azeotropes may be used to separate components of reaction product stream during the production of HCFO-1233xf or of an intermediate reaction stream during the production of 2,3,3,3-tetrafluoropropene (HFO-1234yf).

In embodiments where the azeotrope or azeotrope-like composition includes hydrogen fluoride, 2-chloro-3,3,3-trifluoropropene, and 1,1,2,3-tetrachloropropene, hydrogen fluoride may be provided in an amount from about 3 to about 28 weight percent; 2-chloro-3,3,3-trifluoropropene may be provided in an amount from about 68 to about 93 weight percent; and 1,1,2,3-tetrachloropropene may be provided in an amount from about 2.5 to about 4.3 weight percent. In further embodiments, hydrogen fluoride is present in an amount from about 5.9 to about 25 weight percent; 2-chloro-3,3,3-trifluoropropene is present in an amount from about 72 to about 90.3 weight percent, and 1,1,2,3-tetrachloropropene is present in an amount from about 3.0 to about 3.8 weight percent. It has a boiling point between about 0 to about 61° C. at a pressure between about 15 to about 110 psia. In further embodiments, it has a boiling point of about 0° C. at a pressure of about 16.2 psia; a boiling point of about 24.9° C. at a pressure of about 39.9 psia; and/or a boiling point of about 59.8° C. at a pressure of about 109.7 psia.

In embodiments where the azeotrope or azeotrope-like composition includes hydrogen fluoride, 2-chloro-3,3,3-trifluoropropene, and 1,1,1,2,2-pentafluoropropane, hydrogen fluoride may be provided in an amount from about 3.0 to about 22.0 weight percent; 2-chloro-3,3,3-trifluoropropene may be provided in an amount from about 65.0 to about 83.5 weight percent; and 1,1,1,2,2-pentafluoropropane may be provided in an amount from about 11.1 to about 15.5 weight percent. In further embodiments, hydrogen fluoride may be provided in an amount from about 4.5 to about 20.5 weight percent; 2-chloro-3,3,3-trifluoropropene may be provided in an amount from about 67.4 to about 81 weight percent; and 1,1,1,2,2-pentafluoropropane may be provided in an amount from about 12.1 to about 14.5 weight percent. It has a boiling point between about 0 to about 61° C. as a pressure between about 15 to about 110 psia. In further embodiments, it has a boiling point of about 0° C. at a pressure of about 18.0 psia; a boiling point of about 24.9° C. at a pressure of about 44.8 psia; and a boiling point of about 59.7° C. at a pressure of about 120.0 psia.

In embodiments where the azeotrope or azeotrope-like composition includes 2,3,3,3-tetrachloropropene and hydrogen fluoride; 2,3,3,3-tetrachloropropene may be provided in an amount between about 3 to about 7 wt % and hydrogen fluoride in an amount between about 93 to about 97 wt %. In further embodiments, this binary azeotrope or azeotrope-like composition is formed from about 5 wt % of 2,3,3,3-tetrachloropropene and about 95 wt % of hydrogen fluoride and has a boiling point of about 25° C. at a pressure of about 18 psia The ternary azeotropes of the instant invention may be formed by blending effective amounts of hydrogen fluoride, 2-chloro-3,3,3-trifluoropropene, and either 1,1,2,3-tetrachloropropene or 1,1,1,2,2-pentafluoropropane, using methods defined herein, and the binary azeotrope or azeotrope-like composition from by blending effective amounts of 2,3,3,3-tetrachloropropene and hydrogen fluoride, using methods defined herein.

The azeotrope and azeotrope-like compositions of the present invention may be used in methods for removing 1,1,2,3-tetrachloropropene, 2-chloro-3,3,3-trifluoropropene, 1,1,1,2,2-pentafluoropropane and/or 2,3,3,3-tetrachloropropene from a mixture containing 1,1,2,3-tetrachloropropene, 2-chloro-3,3,3-trifluoropropene, 1,1,1,2,2-pentafluoropropane and/or 2,3,3,3-tetrachloropropene and at least one other component. The method includes adding hydrogen fluoride to the mixture in an amount sufficient to form either of the ternary azeotropes or azeotrope-like compositions or the binary azeotrope discussed herein. Once formed, the azeotrope or azeotrope-like composition(s) is separated from the at least one other component using standard separation techniques, such as distillation. The other components of the mixture may or may not form an azeotrope or azeotrope-like mixture with any of 1,1,2,3-tetrachloropropene, 2-chloro-3,3,3-trifluoropropene, 1,1,1,2,2-pentafluoropropane, 2,3,3,3- tetrachloropropene or combinations thereof. In certain aspects, the at least one other component comprises a halocarbon, which may be a by-product, starting reagent, or intermediate in the process for producing 2,3,3,3-tetrafluoropropene (HFO-1234yf). Such halocarbons may be selected from the group consisting of 2-chloro-1,1,1,2-tetrafluoropropane; 1,1,1,2,3-pentachloropropane; 2,3,3,3-tetrafluoropropene; 2,3-dichloro-3,3-difluoropropene (HCFO-1232xf); 1,2-dichloro-3,3,3-trifluoropropene; 2,3,3-trichloro-3-fluoropropene (HCFO-1231xf); 3,3,3-trifluoropropyne, and combinations thereof.

The present invention also relates to a method for producing 2-chloro-3,3,3-trifluoropropene by, first, reacting a starting material comprising at least one hydrochlorocarbon (e.g. 1,1,2,3-tetrachloropropene and/or 2,3,3,3-tetrachloropropene) and/or hydrochlorofluorocarbon with a fluorinating agent to produce a reaction product comprising 2-chloro-3,3,3-trifluoropropene, hydrogen fluoride, and 1,1,2,3-tetrachloropropene and/or 1,1,1,2,2-pentafluoropropane. The reaction product is then distilled to produce a distillate comprising either or both of the ternary azeotrope-like compositions discussed herein. The distillate is then contacted with one or more substances to separate at least a portion of said ternary azeotrope-like composition from said distillate, i.e. 2-chloro-3,3,3-trifluoropropene, hydrogen fluoride, and either 1,1,2,3-tetrachloropropene or 1,1,1,2,2-pentafluoropropane are separated in an amount sufficient to break said ternary azeotrope-like composition. In certain aspects, this contacting steps includes contacting said distillate with sulfuric acid, a caustic solution or an aqueous system and subsequently removing at least a portion of said hydrogen fluoride from said distillate to produce a purified distillate comprising said 2-chloro-3,3,3-trifluoropropene and either 1,1,2,3-tetrachloropropene or 1,1,1,2,2-pentafluoropropane. The purified distillate is then contacted with an extraction media having a selective affinity for 2-chloro-3,3,3-trifluoropropene relative to 1,1,2,3-tetrachloropropene or 1,1,1,2,2-pentafluoropropane and subsequently separating said 2-chloro-3,3,3-trifluoropropene from said 1,1,2,3-tetrachloropropene or 1,1,1,2,2-pentafluoropropane.

In further embodiments, the present invention relates to methods for fluorinating an organic compound by providing an azeotrope-like composition of 1,1,2,3-tetrachloropropene, 2-chloro-3,3,3-trifluoropropene and hydrogen fluoride; and reacting at least a portion of said 1,1,2,3-tetrachloropropene in the vapor phase with a fluorinating agent to produce at least one fluorinated organic compound. Alternatively, such methods may include providing an azeotrope-like composition consisting essentially of 2,3,3,3-tetrachloropropene and hydrogen fluoride; and reacting at least a portion of said 2,3,3,3-tetrachloropropene in the vapor phase with a fluorinating agent to produce at least one fluorinated organic compound.

Methods of the present invention may also include reducing the boiling point of a hydrochloropropene by blending effective amounts of 1,1,2,3-tetrachloropropene, 2-chloro-3,3,3-trifluoropropene, and hydrogen fluoride to form an azeotrope or azeotrope-like mixture of 1,1,2,3-tetrachloropropene 2-chloro-3,3,3-trifluoropropene and hydrogen fluoride. Alternatively, such methods include blending effective amounts of 2,3,3,3-tetrachloropropene and hydrogen fluoride to form an azeotrope-like mixture of 2,3,3,3-tetrachloropropene and hydrogen fluoride.

Additional embodiments and advantages to the instant invention will be readily apparent to one of skill in the art based on the disclosure provided herein.

DETAILED DESCRIPTION OF THE INVENTION

The present invention relates to ternary and binary azeotropes and azeotrope-like compositions. In certain aspects, the ternary azeotrope and azeotrope-like compositions include 2-chloro-3,3,3-trifluoropropene (1233xf), hydrogen fluoride (HF), and either 1,1,2,3-tetrachloropropene (TCP) or 1,1,1,2,2-pentafluoropropane (HFC-245cb). Binary azeotrope and azeotrope-like compositions include 2,3,3,3-tetrachloropropene and HF. While not limited thereto, one or a combination of these azeotropes may be used to separate components of an reaction stream during the production of a haloolefin, such as HCFO-1233xf or 2,3,3,3-tetrafluoropropene (HFO-1234yf).

As used herein, the term "azeotrope-like" relates to compositions that are strictly azeotropic or that generally behave like azeotropic mixtures. An azeotropic mixture is a system of two or more components in which the liquid composition and vapor composition are equal at the stated pressure and temperature. In practice, this means that the components of an azeotropic mixture are constant-boiling or essentially constant-boiling and generally cannot be thermodynamically separated during a phase change. The vapor composition formed by boiling or evaporation of an azeotropic mixture is identical, or substantially identical, to the original liquid composition. Thus, the concentration of components in the liquid and vapor phases of azeotrope-like compositions change only minimally, if at all, as the composition boils or otherwise evaporates. In contrast, boiling or evaporating non-azeotropic mixtures changes the component concentrations in the liquid phase to a significant degree.

As used herein, the term "consisting essentially of", with respect to the components of an azeotrope-like composition, means the composition contains the indicated components in an azeotrope-like ratio, and may contain additional components provided that the additional components do not form new azeotrope-like systems. For example, azeotrope-like mixtures consisting essentially of three compounds are those that form ternary azeotropes and of two compounds are those that form binary azeotropes, which optionally may include one or more additional components, provided that the additional components do not render the mixture non-azeotropic and do not form an azeotrope with any of the compounds forming the azeotrope.

The term "effective amount," as used herein, refers to the amount of each component which, upon combination with the other component, results in the formation of an azeotrope or azeotrope-like composition of the present invention.

Ternary Azeotrope or Azeotrope-Like Compositions of HCFO-1233xf, TCP, and HF

In one embodiment, the present invention provides 2-chloro-3,3,3-trifluoropropene (HCFO-1233xf), 1,1,2,3-tetrachloropropene (TCP), and hydrogen fluoride in effective amounts to form an azeotropic or azeotrope-like composition. The inventive compositions preferably are ternary azeotropes which consist essentially of combinations of only HCFO-1233xf, TCP and hydrogen fluoride (HF).

In certain embodiments of the foregoing, the ternary azeotrope or azeotrope-like composition of HCFO-1233xf, TCP, and HF is formed when 1233xf is present in an amount from about 68 to about 93 weight percent; TCP is present in an amount from about 2.5 to about 4.3 weight percent; and HF is present in an amount from about 3 to about 28 weight percent. In further embodiments, such a ternary azeotrope or azeotrope-like composition is formed when 1233xf is present in an amount from about 72 to about 90.3 weight percent; TCP is present in an amount from about 3 to about 3.8 weight percent; and HF is present in an amount from about 5.9 to about 25 weight percent.

The ternary azeotrope or azeotrope-like composition of HCFO-1233xf, TCP, and HF has a boiling point between about 0 to about 61° C. and a pressure between about 15 to about 110 psia. In certain aspects, it has a boiling point of about 0° C. at a pressure of about 16.2 psia; a boiling point of about 24.9° C. at a pressure of about 39.9 psia; and/or a boiling point of about 59.8° C. at a pressure of about 109.7 psia.

This azeotrope or azeotrope-like composition may be formed during the process for producing 1233xf by reacting HF with one or a combination starting reagents known for that process, and as discussed in greater detail below. The azeotrope or azeotrope-like composition of the instant invention also may be formed by blending HCFO-1233xf, TCP and hydrogen fluoride (HF) in amounts effective to produce the azeotrope or azeotrope-like composition. To this end, each of these components can be purchased commercially and/or can be produced by methods known in the art, such as those described herein. Any of a wide variety of methods known in the art for combining three or more components to form a composition can be adapted for use in the present methods to produce an azeotrope-like composition. For example, 1233xf, TCP and hydrogen fluoride (HF) can be mixed, blended, or otherwise contacted manually and/or by machine, as part of a batch or continuous reaction and/or process, or via combinations of two or more such steps. In view of the disclosure herein, those of skill in the art will be readily able to prepare azeotrope-like compositions according to the present invention without undue experimentation.

Ternary Azeotrope or Azeotrope-Like Compositions of HCFO-1233xf, HFC-245cb, and HF In another embodiment, the present invention provides 2-chloro-3,3,3-trifluoropropene (HCFO-1233xf), 1,1,1,2,2-pentafluoropropane (HFC-245cb), and hydrogen fluoride in effective amounts to form an azeotropic or azeotrope-like composition. The inventive compositions preferably are ternary azeotropes which consist essentially of combinations of only HCFO-1233xf, HFC-245cb and hydrogen fluoride (HF).

In certain embodiments of the foregoing, the ternary azeotrope or azeotrope-like composition of HCFO-1233xf, HFC-245cb, and HF is formed when HCFO-1233xf is present in an amount from about 65 to about 83.5 weight percent; HFC-245cb is present in an amount from about 11.1 to about 15.5 weight percent; and HF is present in an amount from about 3 to about 22 weight percent. In further embodiments, such a ternary azeotrope or azeotrope-like composition is formed when 1233xf is present in an amount from about 67.4 to about 81 weight percent; 245cb is present in an amount from about 12.1 to about 14.5 weight percent; and HF is present in an amount from about 4.5 to about 20.5 weight percent.

The ternary azeotrope or azeotrope-like composition HCFO-1233xf, HFC-245cb, and HF has a boiling point between about 0 to about 61° C. and a pressure between about 15 to about 110 psia. In certain aspects, it has a boiling point of about 0° C. at a pressure of about 18.0 psia; a boiling point of about 24.9° C. at a pressure of about 44.8 psia; and/or a boiling point of about 59.8° C. at a pressure of about 120.0 psia.

This azeotrope or azeotrope-like composition may be formed during the process for producing HCFO-1233xf by reacting HF with one or a combination starting reagents known for that process and as discussed in greater detail below. Alternatively, the azeotrope or azeotrope-like composition of the instant invention may be formed by blending HCFO-1233xf, HFC-245cb, and HF in amounts effective to produce the azeotrope or azeotrope-like composition. To this end, each of these components can be purchased commercially and/or can be produced by methods known in the art, such as those described herein. Any of a wide variety of methods known in the art for combining three or more components to form a composition can be adapted for use in the present methods to produce an azeotrope-like composition. For example, HCFO-1233xf, HFC-245cb, and HF can be mixed, blended, or otherwise contacted manually and/or by machine, as part of a batch or continuous reaction and/or process, or via combinations of two or more such steps. In view of the disclosure herein, those of skill in the art will be readily able to prepare azeotrope-like compositions according to the present invention without undue experimentation.

Binary Azeotrope or Azeotrope-Like Compositions of 2,3,3,3-Tetrachloropropene and HF In further embodiments, the present invention provides 2,3,3,3-tetrachloropropene and hydrogen fluoride in effective amounts to form an azeotropic or azeotrope-like composition. The inventive compositions preferably are binary azeotropes which consist essentially of combinations of only 2,3,3,3-tetrachloropropene and hydrogen fluoride (HF).

In certain embodiments of the foregoing, the binary azeotrope or azeotrope-like composition of 2,3,3,3-tetrachloropropene and HF is formed when 2,3,3,3-tetrachloropropene is present in an amount from about 3 to about 7 weight percent and HF is present in an amount from about 93 to about 97 weight percent. In further embodiments, such a binary azeotrope or azeotrope-like composition is formed when 2,3,3,3-tetrachloropropene is present in an amount of about 5 weight percent and HF is present in an amount of about 95 weight percent.

The binary azeotrope or azeotrope-like composition of 2,3,3,3-tetrachloropropene and HF has a boiling point of about 25° C. at a pressure of about 18 psia.

This azeotrope or azeotrope-like composition may be formed during the process for producing 1233xf by reacting HF with one or a combination starting reagents known for that process and as discussed in greater detail below. Alternatively, the azeotrope or azeotrope-like composition of the instant invention may be formed by blending 2,3,3,3-tetrachloropropene and HF in amounts effective to produce the azeotrope or azeotrope-like composition. To this end, each of these components can be purchased commercially and/or can be produced by methods known in the art, such as those described herein. Any of a wide variety of methods known in the art for combining three or more components to form a composition can be adapted for use in the present methods to produce an azeotrope-like composition. For example, 2,3,3,3-tetrachloropropene and HF can be mixed, blended, or otherwise contacted manually and/or by machine, as part of a batch or continuous reaction and/or process, or via combinations of two or more such steps. In view of the disclosure herein, those of skill in the art will be readily able to prepare azeotrope-like compositions according to the present invention without undue experimentation.

Methods of Use

While not limited thereto, in one aspect the ternary and/or binary azeotropes or azeotrope-like compositions of the instant invention may be formed and used to isolate unreacted starting materials, reaction intermediates, and/or products or by-products used or formed during the production of certain hydrofluorocarbons such as HCFO-1233xf and/or HFO-1234yf. HCFO-1233xf is a known intermediate in the production of HFO-1234yf. Its production is well known in the art and is described in U.S. Applications 20070007488, 20070197842, and 20110004035, the contents of which are incorporated herein by reference. In one non-limiting example, tetrachloropropene- or penta-chloropropane reagents (e.g. 1,1,2,3-tetrachloropropene and/or 2,3,3,3-tetrachloropropene and/or 1,1,1,2,3-pentachloropropane) are fluorinated with hydrogen fluoride in a catalytic liquid or vapor phase reaction. Its product stream can include unreacted starting reagents, HCFO-1233xf, over-fluorinated by-products (e.g. HFC-245cb) and other reaction intermediates, impurities and/or by-products. The ternary and/or binary azeotrope or azeotrope-like compositions of the present invention may be used for separation of the product stream into its component parts, which may be further processed for HFO-1234yf production, or otherwise recycled within the fluorination reaction.

In one aspect, the azeotrope or azeotrope-like compositions are formed during the reaction process or, otherwise, by adding an effective amount of hydrogen fluoride (or one of the other azeotropic components) to the product stream to form one or more of the azeotropes identified herein. Thereafter, the azeotropic or azeotrope-like composition is separated from the product stream using standard separation means, for example by distillation.

While not limiting to the invention, in one aspect the azeotropic or azeotrope-like compositions of the HCFO-1233xf/TCP/HF or 2,3,3,3-tetrachloropropene and HF may be used to isolate unreacted starting reagents from the desired product, HCFO-1233xf. To this end, it is formed as a result of the reaction process or hydrogen fluoride (or another of the azeotropic components) may be added to the reaction product stream, as necessary, to form either or both the HCFO-1233xf/TCP/HF and 2,3,3,3-tetrachloropropene/HF azeotrope or azeotrope-like composition. The azeotrope(s) are then separated and isolated from the product stream using standard separation means, such as by distillation. The distillate may then be contacted with sulfuric acid, a caustic solution, or aqueous system to remove hydrogen fluoride. The remaining components (e.g. HCFO-1233xf/TCP or 2,3,3,3-tetrachloropropene) may be isolated using standard separate or extraction methods. With respect to HCFO-1233xf/TCP, the purified distillate may be contacted with an extraction media having a selective affinity for HCFO-1233xf relative to 1,1,2,3-tetrachloropropene. The isolated HCFO-1233xf may be fed forward for further fluorination in the production of HFO-1234yf. The TCP and/or 2,3,3,3-tetrachloropropene may then be recycled back to the fluorinated for further processing.

The azeotrope of HCFO-1233xf/HFC-245cb/HF also may be recovered from the product stream using one or more of the techniques discussed above. To this end, the azeotrope is formed as a result of the reaction process or hydrogen fluoride (or another of the azeotropic components) may be added to the reaction product stream, as necessary, to form either or both the azeotrope or azeotrope-like composition. The azeotrope is then separated and isolated from the product stream using standard techniques, e.g. distillation. The distillate contacted with sulfuric acid, a caustic solution, or aqueous solution to remove hydrogen fluoride. The remaining components (e.g. HCFO-1233xf/HFC-245cb) may be isolated using standard separation or extraction methods. For example, the purified distillate may be contacted with an extraction media having a selective affinity for HCFO-1233xf relative to HFC-245cb so as to separate the two compounds. HCFO-1233xf may be fed forward for further fluorination in the production of HFO-1234yf. HFC-245cb can be fed forward as a crude first intermediate in the production of 1234yf. Thus, as disclosed in U.S. Application No. 20070197841, 20090240090 and 20090203945, the contents of which are incorporated herein by reference, HFC-245cb can be dehydrohalogenated using a dehydrohalogenation agent known in the art.

The reagents, intermediates, by-products, or impurities of any of the above reaction streams may or may not form alternative azeotrope or azeotrope-like mixtures with any of HFCO-1233xf, TCP, HFC-245cb, HF or 2,3,3,3-tetrachloropropene, individually or in a mixture. Typical impurities or by-products include other halocarbons which may be miscible with HCFO-1233xf and which are known to be reactants for or be produced during the manufacture of HFO-1234yf. Such halocarbons include, but are not limited to, 2-chloro-1,1,1,2-tetrafluoropropane; 1,1,1,2,3-pentachloropropane; 2,3,3,3-tetrafluoropropene; 2,3-dichloro-3,3-difluoropropene (HCFO-1232xf); 1,2-dichloro-3,3,3-trifluoropropene; 2,3,3-trichloro-3-fluoropropene (HCFO-1231xf); 3,3,3-trifluoropropyne and combinations thereof.

In certain embodiments, the azeotrope or azeotrope-like compositions described herein are useful intermediates derived from during synthesis of certain hydrofluoroolefins, such as 2,3,3,3-tetrafluoropropene (HFO-1234yf). For example, where 2,3,3,3-tetrachloropropene and HF are introduced into a reactor during a HCFO-1233xf (intermediate) synthesis reaction, at least a portion of these components form an azeotrope which subsequently can be recovered from the associated reaction product stream.

In further embodiments of the present invention, methods for reducing the boiling point of a hydrochloropropene are provided wherein the method comprises blending effective amounts of TCP, 1233xf and HF to form an azeotrope or azeotrope-like mixture consisting essentially of TCP, HCFO-1233xf and HF. Lowering the boiling point of TCP is advantageous when the TCP is used as a reactant in a vapor phase fluorination reaction. More particularly, lowering the boiling point facilitates vaporization of the compound and, thus, helps prevent decomposition of the compound and also reduces the amount of energy required by the fluorination process.

Accordingly, also provided is a method for fluorinating an organic compound comprising (a) providing an azeotrope-like composition consisting essentially of TCP, HCFO-1233xf and HF; and (b) reacting at least a portion of said TCP in the vapor phase with a fluorinating agent to produce at least one fluorinated organic compound, preferably a hydrochlorofluoroolefin, more preferably a chlorotrifluoropropene, and even more preferably 2-chloro-3,3,3-trifluoropropene.

In even further embodiments of the present invention, methods for reducing the boiling point of a hydrochloropropene are provided wherein the method comprises blending effective amounts of 2,3,3,3-tetrachloropropene and HF to form an azeotrope-like mixture consisting essentially of 2,3,3,3-tetrachloropropene and HF. Lowering the boiling point of 2,3,3,3-tetrachloropropene is advantageous when the 2,3,3,3-tetrachloropropene is used as a reactant in a vapor phase fluorination reaction. More particularly, lowering the boiling point facilitates vaporization of the compound and, thus, helps prevent decomposition of the compound and also reduces the amount of energy required by the fluorination process.

Accordingly, also provided is a method for fluorinating an organic compound comprising (a) providing an azeotrope-like composition consisting essentially of 2,3,3,3-tetrachloropropene and HF; and (b) reacting at least a portion of said 2,3,3,3-tetrachloropropene in the vapor phase with a fluorinating agent to produce at least one fluorinated organic compound, preferably a hydrofluoroolefin, more preferably a tetrafluoropropene, and even more preferably a 2,3,3,3-tetrafluoropropene.

The following non-limiting examples serve to illustrate the invention.

EXAMPLES

Example 1

Ternary Azeotrope or Azeotrope-Like Composition of HCFO-1233xf, TCP, and HF

A mixture of 4 wt % TCP and 96 wt % HCFO-1233xf was prepared in a vessel. Previously degassed HF was then added in stepwise increments until the overall mixture contained 25 wt % HF. At each increment the temperature was maintained 0, 25 and 60° C. The mixture was allowed to reach equilibrium at each temperature and the pressure was recorded. The experimental pressures and temperatures are given in Table 1. Table 1 shows that at HF wt %>5.9 the pressures are nearly constant indicating the formation of a heterogeneous azeotrope-like mixture.

TABLE 1

PTx measurements of TCP, HCFO-1233xf and HF

| HF, wt % | Temp, ° C. | | |
|---|---|---|---|
| | 0 | 24.9 | 59.8 |
| 0.0 | 8.7 | 22.2 | 63.1 |
| 5.9 | 14.8 | 38.0 | 108.5 |
| 9.4 | 15.4 | 38.5 | 109.4 |
| 14.8 | 16.2 | 39.9 | 109.7 |
| 19.4 | 16.3 | 40.1 | 108.7 |
| 25.0 | 16.3 | 39.9 | 109.8 |

Example 2

Ternary Azeotrope or Azeotrope-Like Composition of HCFO-1233xf, TCP, and HF

A mixture of 3.0 wt % TCP, 72.0 wt % HCFO-1233xf and 25.0 wt % HF was maintained at 21° C. Since this mixture forms a heterogeneous azeotrope the azeotropic composition can be determined by sampling the vapor phase. The HF in the vapor phase was sampled and analyzed. The azeotropic composition was determined to be 14.0 wt % HF at 21° C.

Example 3

Ternary Azeotrope or Azeotrope-Like Composition of HCFO-1233xf, HFC-245cb, and HF A mixture of 15.2 wt % HFC-245cb and 84.8 wt % HCFO-1233xf was prepared in a vessel. Previously degassed HF was then added in stepwise increments until the overall mixture contained 20.5 wt % HF. At each increment the temperature was maintained 0, 25 and 60° C. The mixture was allowed to reach equilibrium at each temperature and the pressure was recorded. The experimental pressures and temperatures are given in Table 2. Table 2 shows that at HF wt %>4.5 the pressures are nearly constant indicating the formation of a heterogeneous azeotrope-like mixture.

TABLE 2

PTx measurements of HFC-245cb, HCFO-1233xf, and HF

| HF, wt % | Temp, ° C. | | |
|---|---|---|---|
| | 0 | 24.9 | 59.7 |
| 0.0 | 12.1 | 29.8 | 79.0 |
| 4.5 | 18.1 | 44.5 | 119.7 |
| 11.2 | 18.0 | 44.8 | 120.0 |
| 20.5 | 17.9 | 44.8 | 121.7 |

Example 4

Ternary Azeotrope or Azeotrope-Like Composition of HCFO-1233xf, HFC-245cb, and HF A mixture of 67.5 wt % HCFO-1233xf, 12.0 wt % HFC-245cb and 20.5 wt % HF was maintained at 21° C. Since this mixture forms a heterogeneous azeotrope the azeotropic composition can be determined by sampling the vapor phase. The HF in the vapor phase was sampled and analyzed. The azeotropic composition was determined to be 11.8 wt % HF at 24° C. and 43 psia.

Example 5

Binary Azeotrope or Azeotrope-Like Composition of 2,3,3,3-tetrachloropropene and HF A mixture of 2,3,3,3-tetrachloropropene and HF is combined in a vessel. The system of 2,3,3,3-tetrachloropropene and HF form a heterogeneous azeotrope. Since this is a heterogeneous azeotrope the azeotropic composition can be determined by analyzing the vapor space composition. The vapor space is sampled at 25° C. and the azeotropic composition of HF is determined to be 95 wt % at about 18 psia.

What is claimed is:

1. A ternary azeotrope or azeotrope-like composition consisting essentially of hydrogen fluoride, 2-chloro-3,3,3-trifluoropropene, and a third component selected from the group consisting of 1,1,2,3-tetrachloropropene and 1,1,1,2,2-pentafluoropropane, wherein
   when the third component is 1,1,2,3-tetrachloropropene, hydrogen fluoride is present in an amount from about 3.0 to about 28.0 weight percent, 2-chloro-3,3,3-trifluoropropene is present in an amount from about 68.0 to about 93.0 weight percent, and 1,1,2,3-tetrachloropropene is present in an amount from about 2.5 to about 4.3 weight percent, and
   when the third component is 1,1,1,2,2-pentafluoropropane, hydrogen fluoride is present in an amount, from about 3.0 to about 22.0 weight percent, 2-chloro-3,3,3-trifluoropropene is present in an amount from about 65.0 to about 83.5 weight percent, and 1,1,1,2,2-pentafluoropropane is present in an amount from about 11.1 to about 15.5 weight percent.

2. The ternary azeotropic or azeotrope-like composition of claim 1 wherein the third component is 1,1,2,3-tetrachloropropene.

3. The ternary azeotropic or azeotrope-like composition of claim 2 wherein hydrogen fluoride is present in an amount from about 5.9 to about 25 weight percent; 2-chloro-3,3,3-trifluoropropene is present in an amount from about 72 to about 90.3 weight percent, and 1,1,2,3-tetrachloropropene is present in an amount from about 3.0 to about 3.8 weight percent.

4. The ternary azeotropic or azeotrope-like composition of claim 2 having a boiling point between about 0 to about 61° C. at a pressure between about 15 to about 110 psia.

5. The ternary azeotropic or azeotrope-like composition of claim 2 having a boiling point of about 0° C. at a pressure of about 16.2 psia.

6. The ternary azeotropic or azeotrope-like composition of claim 2 having a boiling point of about 24.9° C. at a pressure of about 39.9 psia.

7. The ternary azeotropic or azeotrope-like composition of claim 2 having a boiling point of about 59.8° C. at a pressure of about 109.7 psia.

8. The ternary azeotropic or azeotrope-like composition of claim 1 wherein the third component is 1,1,1,2,2-pentafluoropropane.

9. The ternary azeotropic or azeotrope-like composition of claim 8 wherein hydrogen fluoride is present in an amount from about 4.5 to about 20.5 weight percent; 2-chloro-3,3,3-trifluoropropene is present in an amount from about 67.4 to about 81 weight percent, and 1,1,1,2,2-pentafluoropropane is present in an amount from about 12.1 to about 14.5 weight percent.

10. The ternary azeotropic or azeotrope-like composition of claim 8 having a boiling point between about 0 to about 61° C. at a pressure between about 15 to about 110 psia.

11. The ternary azeotropic or azeotrope-like composition of claim 8 having a boiling point of about 0° C. at a pressure of about 18.0 psia.

12. The ternary azeotropic or azeotrope-like composition of claim 8 having a boiling point of about 24.9° C. at a pressure of about 44.8 psia.

13. The ternary azeotropic or azeotrope-like composition of claim 8 having a boiling point of about 59.7° C. at a pressure of about 120.0 psia.

* * * * *